(12) United States Patent
Tanaka et al.

(10) Patent No.: US 9,119,903 B2
(45) Date of Patent: Sep. 1, 2015

(54) POROUS COMPOSITE WITH GRADED BIOABSORBABILITY, ARTIFICIAL BONE USING THE SAME, AND MANUFACTURING METHOD THEREOF

(75) Inventors: Junzo Tanaka, Tokyo (JP); Toshiyuki Ikoma, Tokyo (JP); Tomohiko Yoshioka, Tokyo (JP); Takashi Yoshida, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 71 days.

(21) Appl. No.: 14/130,841

(22) PCT Filed: Jul. 4, 2012

(86) PCT No.: PCT/JP2012/067113
§ 371 (c)(1),
(2), (4) Date: Jan. 3, 2014

(87) PCT Pub. No.: WO2013/005778
PCT Pub. Date: Jan. 10, 2013

(65) Prior Publication Data
US 2014/0142717 A1    May 22, 2014

(30) Foreign Application Priority Data
Jul. 4, 2011   (JP) .................................. 2011-148123

(51) Int. Cl.
| A61F 2/28 | (2006.01) |
| A61L 27/58 | (2006.01) |
| A61L 27/42 | (2006.01) |
| A61L 27/46 | (2006.01) |
| A61L 27/50 | (2006.01) |
| A61L 27/56 | (2006.01) |

(Continued)

(52) U.S. Cl.
CPC .................. *A61L 27/58* (2013.01); *A61F 2/28* (2013.01);*A61L 27/425* (2013.01); *A61L 27/46* (2013.01); ; *A61L 27/50* (2013.01); *A61L 27/56* (2013.01); *A61L 2430/02* (2013.01)

(58) Field of Classification Search
CPC .......... A61L 27/58; A61F 2/28; A61F 2/3067
See application file for complete search history.

(56) References Cited

U.S. PATENT DOCUMENTS

2006/0121609 A1   6/2006 Yannas et al.
2009/0149634 A1   6/2009 Shoji et al.

FOREIGN PATENT DOCUMENTS

| EP | 1 437 148 A1 | 7/2004 |
| JP | 2001-286494 | 10/2001 |
| JP | 2007-098118 | 4/2007 |
| JP | 2008-018163 | 1/2008 |
| JP | 2010-273847 A | 12/2010 |

OTHER PUBLICATIONS

Extended European Search Report, Feb. 9, 2015, EP Patent Application No. 1287115.6, 8 pages.
Yunoki, et al.; Effects of increased collagen-matrix density on the mechanical properties and in vivo absorbability of hydroxyapatite-collagen composites as artificial bone materials; Biomedical Materials; 6 (2011), vol. 6, No. 1, p. 015012.
International Search Report of PCT/JP2012/067113, mailed Jul. 31, 2012.

*Primary Examiner* — Jason-Dennis Stewart
(74) *Attorney, Agent, or Firm* — Kilpatrick Townsend & Stockton LLP (57) ABSTRACT

The object of the present invention is to provide a calcium phosphate-collagen fiber composite which has an excellent mechanical property, can induce bone replacement by rapid bone remodeling, and can be used in a high-load region. The object can be solved by a porous composite comprising a calcium phosphate crystal and a collagen fiber at a weight ratio of 80:20 to 20:80, wherein (1) a bioabsorbability of the porous composite is graded, and (2) the density of the porous composite determined by gravimetric method is 300 to 1500 $mg/cm^3$.

14 Claims, 3 Drawing Sheets

POROUS COMPOSITE WITH GRADED BIOABSORBABILITY, ARTIFICIAL BONE USING THE SAME, AND MANUFACTURING METHOD THEREOF

CROSS-REFERENCE TO RELATED APPLICATIONS

This application is a national phase application under 35 U.S.C. 371 claiming priority to PCT/JP2012/067113, filed Jul. 4, 2012, which application claims priority to JP 2011-148123, filed Jul. 4, 2011, the teachings of which are hereby incorporated by reference in their entireties for all purposes.

TECHNICAL FIELD

The present invention relates to a porous composite with graded bioabsorbability, an artificial bone using the same, and a manufacturing method thereof. According to the present invention, it is possible to provide artificial bone capable of promoting regeneration of bone tissue without loss of strength in vivo.

BACKGROUND ART

In the bone tissue, collagen and hydroxyapatite interact on a nano level, and then hydroxyapatite is aligned along the collagen fibers to obtain assembly thereof. Further, a hierarchic structure is formed by the assembly. The bone tissue exhibits excellent mechanical characteristics through the hierarchic structure and an interaction between collagen fibers.

In the case of loss of bone tissue, an autologous bone graft using an iliac bone, fibula or the like of a patient is mainly performed as a treatment thereof. However, in the autologous bone graft, a secondary operation is required, and thus it is a high burden on the patients. Further, an infection sometimes occurs in the exenteration region of the secondary operation. Furthermore, the amount of the autologous bone to be collected is limited. Thus, an attempt to use an artificial bone instead of the autologous bone, or an attempt to supply an artificial bone (i.e. filling material) to a deficient part of the autologous bone, has been made.

Hitherto, as the artificial bone, ceramic-based artificial bone made of calcium phosphate with an osteoconduction is used. However, a postoperative break and a poor handling due to a brittleness which are typical characteristics of ceramic, have been pointed out in the clinical site. Further, the artificial bone requires specific physiological properties, such as a biocompatibility and an osteoconductive property. The autologous bone metabolizes and thus alternates between resorption and ossification. However, the artificial bone made of apatite can hardly dissolve in a body, and thus almost permanently remains therein. The artificial bone used in bone regeneration requires a property for fusing to bone tissue and promoting bone regeneration, in addition to bone-seeking. That is, the artificial bone requires the osteoconductive property and a bioactivity, in order to be absorbed gradually after applying to the body, become incorporated into a bone regeneration cycle (bone remodeling), and be replaced with the individual's bone tissue.

In view of the above points, a calcium phosphate-collagen composite wherein collagen is added to calcium phosphate, is desired as the artificial bone for bone regeneration. The calcium phosphate-collagen composite has osteoconduction and exhibits a flexibility which is deficient in the conventional ceramic. Therefore, the calcium phosphate-collagen composite is studied for practical use, as a scaffold material for bone regeneration. However, the calcium phosphate-collagen composite is too soft, compared to the conventional material made of apatite, and thus it easily becomes deformed by a lower load. Therefore, a problem emerges where the calcium phosphate-collagen composite cannot be applied to a high-load region as a bone regeneration template.

The development of the calcium phosphate-collagen composite is oriented in two directions. One direction is to attach weight to the osteoconductive property as the scaffold material for bone regeneration, and the other direction is to attach weight to a mechanical strength as the template of bone regeneration. As an example of the former calcium phosphate-collagen composite, the patent literature 1 discloses that a dried apatite-collagen composite fiber is gamma-irradiated to obtain a porous material wherein a half-life of strength is shortly adjusted. On the other hand, as an example of the latter calcium phosphate-collagen composite, the patent literature 2 discloses that a concentration of collagen fibers is increased and thereby the density thereof may rise to 130 to 600 $mg/cm^3$ in order to obtain a calcium phosphate-collagen fiber composite having excellent mechanical properties such as a high strength and a high elasticity close to those of autologous bone in the body.

However, a calcium phosphate-collagen composite having an excellent mechanical property has not been developed. That is, a calcium phosphate-collagen composite which can be rapidly replaced with the patient's own bone tissue via bone remodeling and can be used in a high-load region as the scaffold material for bone regeneration, has not been developed.

CITATION LIST

Patent Literature

[Patent literature 1] Japanese Unexamined Patent Publication (Kokai) No. 2009-132601
[Patent literature 2] Japanese Unexamined Patent Publication (Kokai) No. 2010-273847
[Patent literature 3] Japanese Unexamined Patent Publication (Kokai) No. 2001-286494
[Patent literature 4] Japanese Unexamined Patent Publication (Kokai) No. 2008-18163
[Patent literature 5] Japanese Unexamined Patent Publication (Kokai) No. 2007-98118

SUMMARY OF INVENTION

Technical Problem

According to the porous composite wherein the first piece and second piece can be cut out of the porous composite and the ratio of bioabsorbabilities thereof is 1.5 times or more, the inventors of the present invention found that the calcium phosphate-collagen fiber composite with an excellent mechanical property, which can induce bone replacement by a rapid bone remodeling and can be used in a high-load region in regenerating bone tissue, may be obtained.

As mentioned above, one of the conventional calcium phosphate-collagen composites mainly has the osteoconductive property as the scaffold material for bone regeneration. Further, the other of the conventional calcium phosphate-collagen composites mainly has the mechanical strength as the bone template. Therefore, a calcium phosphate-collagen composite for artificial bone, satisfying both the induction of bone replacement and the mechanical strength, has not existed.

As an apatite or calcium phosphate-based artificial bone without collagen, the artificial bone-combining parts having different porosities from one another (Patent literature 3), or the artificial bone having gradated porosity (Patent literature 4) is disclosed. However, in these artificial bones, the bioabsorbability for inducing the bone replacement was not taken into consideration.

The object of the present invention is to provide a calcium phosphate-collagen fiber composite which has an excellent mechanical property, can induce bone replacement by rapid bone remodeling, and can be used in a high-load region.

Solution to Problem

The present inventors have conducted intensive studies into the calcium phosphate-collagen composite with an excellent mechanical property, which can induce bone replacement by rapid bone remodeling and can be used in a high-load region; and as a result, found that the above problem can be solved by continuously or discontinuously varying the bioabsorbability. That is, the present inventors found that the porous composite with h graded bioabsorbability is useful as artificial bone. Further, the present inventors found that the gradation of bioabsorbability can be controlled by cross-linking. For example, cross-link density can be controlled by a glutaraldehyde vapor deposition method using volatilization and diffusion of glutaraldehyde. Furthermore, a material permeability of irradiation is excellent, and thus homogeneous cross-linking into the material can be carried out. That is, the present inventors found that the cross-link density can be controlled gradually by controlling an amount of permeable gamma radiation using a tapered member, and thus the porous composite with graded bioabsorbability can be manufactured by these cross-linking methods.

The present invention is based on the above findings.

Namely, the present invention relates to:

[1] a porous composite comprising a calcium phosphate crystal and a collagen fiber at a weight ratio of 80:20 to 20:80, wherein (1) a bioabsorbability of the porous composite is graded, and (2) the density of the porous composite determined by gravimetric method is 300 to 1500 mg/cm$^3$;

[2] the porous composite of item [1], wherein the gradation of bioabsorbability is represented by a strength ratio of two points in the porous composite, determined by an indentation test using a cylindrical probe with a diameter of 2 mm, and the strength ratio of the two points at a distortion rate of 30% is 1.5 or more;

[3] the porous composite of item [1], wherein the bioabsorbability is continuously or discontinuously varied, the first piece of the composite having a higher bioabsorbability and the second piece of the composite having a lower bioabsorbability can be cut out of the porous composite, the gradation of bioabsorbability is represented by a ratio of bioabsorbabilities of the first piece to the second piece, and the ratio is 1.5 times or more;

[4] the porous composite of item [3], wherein the bioabsorbability is a biodegradation rate determined by collagenase digestion, the biodegradation rate is represented by the following equation (I):

$$\text{Biodegradation rate} = (W_0 - W_t)/W_0 \times 100 \quad \text{(I)}$$

(wherein $W_0$ and $W_t$ is both a dry weight before immersion and after immersion respectively, when the pieces of the porous composite are immersed in a collagenase solution of 2 unit/mL for 6 hours or in a collagenase solution of 200 units/mL for 30 minutes), the first piece is cut out of a region of 30% by weight of the porous composite having a higher biodegradation rate, the second piece is cut out of a region of 30% by weight of the porous composite having a lower biodegradation rate, and a ratio of biodegradation rates of the first piece to the second piece is 1.5 times or more;

[5] the porous composite of item [3], wherein the bioabsorbability is denoted by a swelling ratio, the swelling ratio is represented by the following equation (II):

$$\text{Swelling ratio} = (W_w - W_d)/W_d \times 100 \quad \text{(II)}$$

(wherein $W_d$ and $W_w$ is a dry weight ($W_d$) before immersion and a wet weight ($W_w$) after immersion respectively, when the pieces of the porous composite are immersed in a phosphate-buffered saline for 24 hours), the first piece is cut out of a region of 30% by weight of the porous composite having a higher swelling ratio, the second piece is cut out of a region of 30% by weight of the porous composite having a lower swelling ratio, and a ratio of swelling ratios of the first piece to the second piece is 1.5 times or more;

[6] the porous composite of items [1] to [5], wherein calcium phosphate is at least one calcium phosphate selected from the group consisting of hydroxyapatite, monocalcium phosphate anhydrous, monocalcium phosphate hydrate, dicalcium phosphate anhydrous, dicalcium phosphate hydrate, octacalcium phosphate, and tricalcium phosphate;

[7] an artificial bone comprising the porous composite of items [1] to [6];

[8] a method for preparing a porous composite, comprising the steps of:

(A) forming a porous material containing calcium phosphate and collagen, and (B) cross-linking the porous material in a gradient manner through a cross-linking treatment capable of varying cross-link density, to obtain a porous composite having at least two regions wherein the ratio of bioabsorbabilities thereof is 1.5 times or more;

[9] the method for preparing a porous composite of item [8], wherein the porous material forming step (A) comprises the steps of:

(1) crystallizing calcium phosphate, to obtain a suspension of crystals or surface-modified crystals of calcium phosphate, (2) forming a collagen fibril from a soluble collagen in a collagen solution, to obtain a collagen fiber suspension, (3) mixing the collagen fibers suspension and the suspension of calcium phosphate crystals, to obtain a mixed suspension of calcium phosphate crystals and collagen fibers, and (4) forming the porous material from the mixed suspension of calcium phosphate crystals and collagen fibers;

[10] the method for preparing a porous composite of item [8], wherein the porous material forming step (A) is a step of mixing calcium phosphate-collagen composite fibers, and a buffered solution, to gelate and form a porous material;

[11] the method for preparing a porous composite of items [8] to [10], wherein the cross-linking in the gradient cross-linking step (B) is a cross-linking by a glutaraldehyde vapor deposition method, and a diffusion amount of glutaraldehyde gas into the porous material is varied, to prepare the porous composite having at least two regions wherein the ratio of bioabsorbabilities thereof is 1.5 times or more;

[12] the method for preparing a porous composite of items [8] to [10], wherein the cross-linking in the gradient cross-linking step (B) is a cross-linking via irradiation, and the amount of irradiation to the porous material is varied under wet conditions, to prepare the porous composite having at least two regions wherein the ratio of bioabsorbabilities thereof is 1.5 times or more;

[13] the method for preparing a porous composite of [12], wherein the surface of the calcium phosphate crystal is modified with molecules with vinyl groups;

[14] the method for preparing a porous composite according to claim 12, wherein calcium phosphate is at least one calcium phosphate selected from the group consisting of hydroxyapatite, monocalcium phosphate anhydrous, monocalcium phosphate hydrate, dicalcium phosphate anhydrous, dicalcium phosphate hydrate, octacalcium phosphate, and tricalcium phosphate.

Advantageous Effects of Invention

According to the porous composite of the present invention, the bone replacement can be induced by rapid bone remodeling, and the porous composite can be applied to a high-load region due to excellent mechanical properties. That is, the porous composite has a composition and physical properties similar to the biological hard tissue. Thus, when the porous composite is implanted into the body, it can control a region wherein the bone replacement is rapidly induced by bone remodeling, and a region wherein the bone tissue is regenerated therearound by remaining in the body over a long period of time. That is, the porous composite of the present invention is a functionally-graded material capable of promoting the regeneration of bone tissue without loss of strength in vivo. The porous composite of the present invention can be used as a biological material such as a filling material for bone or a scaffold material for regenerative medicine. Further, according to the artificial bone using the porous composite of the present invention, bone tissue or bone-marrow tissue can be regenerated in a bone loss region.

Further, according to the method for preparing a porous composite of the present invention, the calcium phosphate-collagen fiber composite for artificial bone, which satisfies the induction of bone replacement and the mechanical strength, can be manufactured by controlling the cross-linking of the calcium phosphate-collagen fiber composite.

DESCRIPTION OF EMBODIMENTS

[1] Porous Composite

The porous composite of the present invention comprises a calcium phosphate crystal and a collagen fiber at a weight ratio of 80:20 to 20:80, and it is characterized in that (1) a bioabsorbability of the porous composite is graded, and (2) a density of the porous composite determined by the gravimetric method is 300 to 1500 mg/cm$^3$. Preferably, the bioabsorbability is continuously or discontinuously varied, and a first piece having a higher bioabsorbability and a second piece having a lower bioabsorbability can be cut out of the porous composite, the gradation of bioabsorbability is represented by a ratio of bioabsorbabilities of the first piece to the second piece, and the ratio is 1.5 or more.

The gradation of bioabsorbability can be expressed by a ratio of bioabsorbabilities of two certain points. The ratio is preferably two times or more, more preferably 3 times or more, even more preferably 5 times or more, most preferably 10 times or more. Further, an upper limit is not particularly limited, but preferably 1000 times or less.

(Calcium Phosphate Crystal)

As a calcium phosphate used for calcium phosphate crystal, there may be mentioned a group of compounds such as $Ca(H_2PO_4)_2$, $Ca(H_2PO_4)_2.H_2O$, $CaHPO_4$, $CaHPO_4.2H_2O$, $Ca_3(PO_4)_2$, $Ca_3(PO_4)_2.2H_2O$, $Ca_8H_2(PO_4)_6.5H_2O$, $Ca_3(PO_4)_2$, $Ca_{10}(PO_4)_6(OH)_2$, $Ca_4O(PO_4)_2$, $CaP_4O_{11}$, $Ca(PO_3)_2$, or $Ca_2P_2O_7$. In particular, hydroxyapatite, monocalcium phosphate anhydrous, monocalcium phosphate hydrate, dicalcium phosphate anhydrous, dicalcium phosphate hydrate, octacalcium phosphate, or tricalcium phosphate is preferable, and hydroxyapatite is the most preferable. Hydroxyapatite is one of calcium phosphates which accounts for 60% to 80% of components of bone in a body, and a basic component thereof is a compound represented by the composition formula: $Ca_{10}(PO_4)_6(OH)_2$. A part of Ca contained in hydroxyapatite may be replaced with one or more elements selected from Sr, Ba, Mg, Fe, Al, Y, La, Na, K, H, or the like. Further, a part of $(PO_4)$ may be replaced with one or more elements selected from $VO_4$, $BO_3$, $SO_4$, $CO_3$, $SiO_4$ or the like. Furthermore, a part of (OH) may be replaced with F, Cl, O, $CO_3$ or the like. In addition, a part of these elements may be lacking.

The above calcium phosphate crystal can contain one or more selected from the group of compounds, such as crystal of hydroxyapatite and tricalcium phosphate, crystal of hydroxyapatite and calcium monohydrogen phosphate, crystal of hydroxyapatite and octacalcium phosphate, and the like.

(Collagen)

It is known that about 28 different molecules of collagen exist in tissue of wide range of animals including mammals and a fish. In the collagen which may be used in the porous composite of the present invention, kinds of animals, tissues, ages, or the like of a starting material thereof are not particularly limited. However, for example, a collagen obtained from skin, bone, cartilage, tendon, organ, or the like of mammals (such as bovine, swine, horse, rabbit, mouse, or the like), or birds (such as chicken, or the like), or a collagen obtained from skin, bone, cartilage, fin, scale, organ, or the like, of fish (such as cod, bastard halibut, flatfish, salmon, trout, tuna, mackerel, sea bream, sardines, shark, tilapia, or the like) can be used. Further, a collagen artificially obtained by genetic engineering can be used. In particular, taking into account the use as the artificial bone implanted into the living body, it is preferable to use the collagen derived from a fish which does not have pathogens such as zoonotic virus. Furthermore, when the cross-linking by irradiation is carried out, a steric distance between collagens, or between collagen and apatite at the interface, is important. Therefore, the scale-derived collagen, which can be highly concentrated, is preferable.

As for the collagen, the collagen molecules such as type I collagen to type VIII collagen are well known, and the type I, II, III, and V collagens are fibrillar collagen. The collagen has a characteristic primary structure wherein glycine is found at every third residue, in the amino acid sequence thereof. The repeating sequence is a property of collagen protein and is referred to as a collagen-like sequence. The collagen used in the present invention is limited to the fibrillar collagen. However, a collagen wherein the amino acid residue is subjected to chemical modification such as acetylation, succinylation, maleylation, phthalation, benzoylation, esterification, amidation, guanidination, or the like, can be used.

(Weight Ratio)

The weight ratio of calcium phosphate crystals and collagen fibers comprised in the porous composite of the present invention is preferably 80:20 to 20:80, more preferably 80:20 to 50:50, most preferably 80:20 to 70:30. When the amount of the collagen is less than 20% by weight (the amount of the calcium phosphate crystal is more than 80% by weight), the brittleness of the porous composite is significant. When the amount of the collagen is more than 80% by weight (the amount of the calcium phosphate crystal is less than 20% by weight), the porous composite becomes structurally weakened, and the mechanical strength thereof becomes insufficient. That is to say, when the weight ratio of calcium phosphate crystal and collagen is 80:20 to 20:80, the porous composite having excellent mechanical strength such as flextural breaking strain, flextural elastic modulus, and the excellent bioabsorbability as an artificial bone, can be obtained.

The ratio of calcium phosphate crystal and collagen may be calculated by measuring the ratio of amounts of the calcium phosphate crystal and the collagen in the porous composite. However, it can be calculated from the ratio of calcium phosphate and collagen contained in a mixed suspension of calcium phosphate crystals and collagen fibers in a manufacturing process of the porous composite.

(Bioabsorbability)

The porous composite of the present invention is obtained by combining collagen fibers with calcium phosphate crystal, and characterized in that the bioabsorbability is continuously or discontinuously varied. By the gradient of bioabsorbability, the region wherein the bone replacement can be rapidly induced, and a region with excellent mechanical property wherein the bone tissue can be regenerated therearound by remaining in the body over a long period of time, can exist in one composite. That is, the calcium phosphate crystal-collagen fiber composite for artificial bone satisfying the induction of bone replacement and the mechanical strength can be obtained by the continuous or discontinuous variation of the bioabsorbability. In particular, the region having excellent bioabsorbability has a property of excellent induction of bone replacement. The region resistant to bioabsorbability has an excellent mechanical strength.

An index of bioabsorbability is not particularly limited. For example, the index can be represented by a strength (such as a strength determined by an indentation test, fluxtural breaking strain, and fluxtural elastic modulus), density, cross-link density, swelling ratio, porosity, pore diameter, interconnected pore diameter or biodegradation rate determined by collagenase digestion, or the like. In particular, the strength determined by an indentation test, swelling ratio, or biodegradation rate determined by collagenase digestion is preferable.

When the calcium phosphate crystal and the collagen fiber are homogeneously combined to obtain a porous composite under the same condition, the bioabsorbability in the porous composite may not vary in general. The gradation of bioabsorbability is induced by manufacturing conditions. In particular, it is achieved by a condition of cross-linking as mentioned below. The condition of cross-linking is reflected in the strength determined by an indentation test, swelling ratio, or biodegradation rate determined by collagenase digestion, and thus, these three indexes are preferable as the indexes of bioabsorbability.

For example, the porous composite having the continuously varied bioabsorbability can be obtained by continuously varying the porous composite's condition. For example, it can be obtained by continuously varying the cross-link density as mentioned below.

For example, the porous composite having the discontinuously varied, bioabsorbability can be obtained by layering some porous composites prepared by different manufacturing conditions with each other. Further, it can be obtained by discontinuously varying the cross-link density as mentioned below At least two pieces wherein the ratio of bioabsorbability thereof is 1.5 times or more can be cut out of the porous composite of the present invention. That is, the first piece having higher bio absorbability and the second piece having lower bioabsorbability can be cut out of the porous composite. The first piece and the second piece can be cut out of any region of the porous composite, as long as the ratio of the bioabsorbability is 1.5 times or more. For example, in the case that the porous composite obtained by layering some porous composites having different bioabsorbabilities from one another, the first piece and second piece can be obtained from the different laminated porous composites, respectively. Further, in the case of the porous composite having continuously varied bioabsorbability, a manufacturer can control the cross-linking condition by glutaraldehyde vapor deposition method and cross-linking via irradiation. Therefore, the first and second pieces wherein the ratio of the bioabsorbabilities thereof is 1.5 times or more can be accurately cut out of the porous composite.

Further, people other than the manufacturer can easily define the region containing the first piece having higher bioabsorbability and the region containing the first piece having lower bioabsorbability, as mentioned below. Thus, the first piece and second piece may be cut out of the defined regions.

When the strength ratio of two points determined by the indentation test is used, the indentation test can be carried out without cutting out two pieces. That is to say, the gradation of bioabsorbability can be measured without cutting out two pieces.

(Strength Ratio Determined by Indentation Test)

The strength ratio determined by an indentation test, one of the indexes of bioabsorbability, may be measured as follows. Mechanical strengths in some points of obtained porous composite are measured by an indentation tester. The strength ratio can be obtained by comparing two strengths among some point strengths.

As a method of indentation test, a conventional method may be used. The method is not limited, for example, but the indentation test may be carried out as follows.

The porous composite is immersed in Dulbecco's phosphate buffered saline, and is subjected to indentation testing using a texture analyzer (TA-XTplus). As a cylinder, a cylindrical probe with a diameter of 2 mm (P/2) is used, and measurements are carried out at any point (for example, five points) of the porous composite. For example, the strength ratio of 1.5 or more at a distortion rate of 30% is observed from the obtained mechanical strength.

The mechanical strength of the porous composite is not limited, but preferably 1N to 1600N, more preferably 100N to 1000N, most preferably 300N to 500N.

The strength ratio of two points of the porous composite is not limited, as long as it is 1.5 times or more, preferably 2.0 times or more, more preferably 5.0 times or more. The upper limit of the strength ratio is not limited, but preferably 10 times or less.

(Biodegradation Rate Determined by Collagenase Digestion)

The biodegradation rate determined by collagenase digestion, one of the indexes of the bioabsorbability, can be calculated by the following equation (I).

Equation (I):

$$\text{Biodegradation rate} = (W_0 - W_t)/W_0 \times 100 \quad \text{(I)}$$

(wherein $W_0$ and $W_t$ is a dry weight ($W_0$) before immersion and a dry weight ($W_t$) after immersion respectively, when the pieces of the porous composite are immersed in a collagenase solution of 2 units/mL for 6 hours or in a collagenase solution of 200 units/mL for 30 minutes)

According to the equation (I), it can be confirmed whether or not the ratio of bioabsorbability is 1.5 times or more by measuring the biodegradation rates of the first and second pieces which are cut out of the porous composite.

In particular, a collagenase treatment can be carried out as follows.

A sample piece of about 10 mg (segment; 0.1×0.1×1.0 cm) is obtained from a porous composite by a trephine for biopsy. A Dulbecco's phosphate buffered saline (pH7.2) containing collagenase of 2.0 units (0.01 mg)/mL, or 200 units (1 mg)/mL is prepared, and 3 mL thereof is added to the sample piece(segment) placed in a well of a multi-well plate. The multi well plate is placed in a bioshaker, and the sample piece is reacted 37° C. for 6 hours (2.0 units) or for 0.5 hours (200 units) while shaking. After the reaction, the sample piece is collected and washed by distilled water for 1 hour. The washed sample piece is frozen in a deep freezer at −20° C., and then freeze-dried. A dry weight of the resulting sample is measured and a biodegradation rate is calculated according to the equation (I). The fundamental bioabsorbability is defined by the biodegradation rate in the case that the sample piece (segment) is immersed in the collagenase solution of 2.0 unit/mL for 6 hours. However, when both biodegradation rates of the first piece and the second piece are 5% or less by weight, both pieces are hardly degraded. In this case, the bioabsorbability is defined by the biodegradation rate in the case that the sample piece (segment) is immersed in the collagenase solution of 200 unit/mL for 0.5 hours.

Further, when both biodegradation rates of the first piece and the second piece are 5% or less, or 95% or more even in the above two conditions, the differences of the biodegradation rates cannot be observed. In this case, the biodegradation rate may be obtained by deciding that the immersion time be adjusted to an appropriate length of time between 0.5 and 24 hours.

In the measurement of the biodegradation rate determined by collagenase digestion, the region containing the first piece having higher bioabsorbability, and the region containing the second piece having lower bioabsorbability in the porous composite, can be preliminarily identified by measuring a whole biodegradation rate of the porous composite. For example, the whole biodegradation rate of the porous composite is measured. Then, a region (A) of 10% to 30% by weight from a point with the highest biodegradation rate in the porous composite can be defined as a region wherein the first piece is cut out, and a region (B) of 10% to 30% by weight from a point with the lowest biodegradation rate in the porous composite can be defined as a region wherein the second piece is cut out. The region other than region (A) and region (B) is defined as region (C) with a middle biodegradation rate.

Further, the region (A) may be a region of 10% to 30% by weight from a point with the highest biodegradation rate, but preferably 0% to 20% by weight of region having a higher biodegradation rate, more preferably 0% to 30% by weight of a region having a higher biodegradation rate.

In the present specification, if the ratio of biodegradation rates of at least one combination of the first piece cut out of the region (A) and the second piece cut out of the region (B), is 1.5 times or more, a significant effect of the present invention can be obtained in the porous composite. That is to say, the effect of the present invention can be obtained, if the first and second pieces wherein the ratio of the biodegradation rates thereof is at least 1.5 times or more, can be cut out of one porous composite. However, it is preferable that the ratio of the biodegradation rate is constantly 1.5 times or more in any combination of the first piece cut out of the region (A) and the second piece cut out of the region (B).

Specifically, the definition of region (A) and region (B) is performed as follows.

A Dulbecco's phosphate buffered saline (pH7.2) containing collagenase of 2.0 units (0.01 mg)/mL, or 200 units (1 mg)/mL is prepared, and an appropriate quantity of the solution is added thereto according to a volume of the porous composite. For example, about 50-fold volume of the solution with respect to the volume of the sample, is added. The solution containing the sample is placed in a bioshaker, and the sample is reacted at 37° C. for 1, 3, 12 18 or 24 hours while shaking at 50 rpm. After the reaction, the sample is collected and washed by distilled water for 1 hour. The sample is frozen in a deep freezer at −20° C., and then freeze-dried. A dry weight of the resulting sample is measured and a biodegradation rate is calculated according to the equation (I).

$$\text{Biodegradation rate} = (W_0 - W_t)/W_0 \times 100 \quad \text{(I)}$$

From the biodegradation rates of 1 to 24 hours, the region (A) of 10% to 30% by weight from a point with the highest biodegradation rate, and the region (B) of 10% to 30% by weight from a point with the lowest biodegradation rate, can be determined.

Weights of the first piece and the second piece of the porous composite are not particularly limited, so long as the biodegradation rate thereof may be measured, but preferably 5 to 30 mg, more preferably 5 to 20 mg, most preferably about 10 mg. Further, even if the weights of the first piece and the second piece are different from each other, the biodegradation rates can be measured. However, pieces with about the same weights are preferably used. If the weights thereof are different, the difference therebetween is preferably 5 mg or less, more preferably 2 mg or less.

Figure 1:
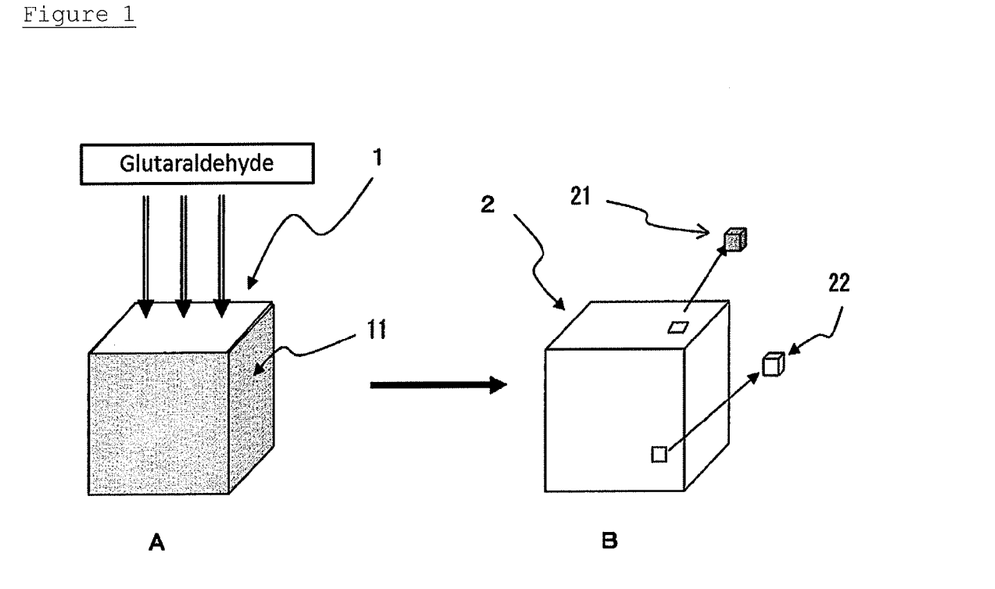
FIG. 1 is a schematic view showing an embodiment of the gradient cross-linking by the glutaraldehyde vapor deposition method.

Further, a shape of the first piece or the second piece is not particularly limited, so long as the biodegradation rate thereof may be measured. For example, the piece with cube(regular hexahedron), cuboid, prismatic column such as a right prism, circular cylinder, or the like, may be used. For example, when the trephine for biopsy is used as described in the examples, the piece of a circular cylinder shape may be obtained. Further, as shown in FIG. 1, pieces of a part resistant to bioabsorbability (cross-linking-advanced part (21)) and a part with excellent bioabsorbability (cross-linking-non-advanced part (22)) are cut out, and the biodegradation rate determined by collagenase digestion can be measured.

A collagenase used in the measurement of the biodegradation rate is not particularly limited. However, a collagenase derived from the genus *Clostridium* can be used.

The biodegradation rate of the region having an ability of rapid bone replacement, i.e. high bioabsorbability, is not particularly limited. However it is preferably 40% or more, more preferably 50% or more, most preferably 60% or more, under the condition that the sample is reacted in 2.0 unit/mL of collagenase solution for 6 hours. When the degradation rate determined by collagenase digestion is 40% or more by weight, the bio absorbability thereof is excellent and the bone replacement may be rapidly induced in the bone regeneration. Therefore, the bone regeneration is easily promoted.

On the other hand, the biodegradation rate of the region having mechanical strength is not particularly limited, but preferably 30% or less, more preferably 15% or less, most preferably 5% or less. When the biodegradation rate determined by collagenase digestion is 30% or less, the porous composite has a sufficient mechanical strength in addition to a biological compatibility and a potential for bone replacement. Thus, the region having mechanical strength remains in a body over a long period of time, and provides a space wherein the bone tissues are regenerated therearound.

Further, the difference between the biodegradation rate of the region having good bioabsorbability and the biodegradation rate of the region having mechanical strength, is not particularly limited, so long as it is 1.5 times or more, but preferably 2 times or more, more preferably 5 times or more, most preferably 10 times or more. Furthermore, an upper limit of the difference is not particularly limited, but preferably 1000 times or less. When the difference between the biodegradation rate of the region having good bioabsorbability and the biodegradation rate of the region having mechanical strength is 1.5 times or more, the artificial bone satisfying the induction of bone replacement and the mechanical strength in a balanced manner is obtainable.

(Swelling Ratio)

The swelling ratio, which is one of the indexes of the bioabsorbability, can be calculated by the following equation (II).

Equation (II):

$$\text{Swelling ratio} = (W_w - W_d)/W_d \times 100 \quad \text{(II)}$$

[wherein $W_d$ and $W_w$ is a dry weight ($W_d$) before immersion and a wet weight ($W_w$) after immersion respectively, when the pieces of the porous composite are immersed in a phosphate buffered saline for 24 hours]

According to the equation (II), it can be confirmed whether or not the ratio of bioabsorbability is 1.5 times or more by measuring the swelling ratios of the first piece and the second piece, which are cut out of the porous composite.

In particular, a measurement method of the swelling ratio is not particularly limited, but the swelling ratio can be measured according to the following method.

A sample piece of about 10 mg (segment) is obtained from porous composite. The sample piece (segment) is immersed in 10 mL of Dulbecco's phosphate buffered saline and allowed to stand at 37° C. for 24 hours. The sample is collected rapidly, and placed on a paper towel (Kimwipe) for 2 minutes. Then a weight thereof is measured. A weight of the resulting sample is measured and a swelling rate is calculated according to the equation (I).

In the measurement of the swelling ratio, the region containing the first piece having higher bioabsorbability, and the region containing the second piece having lower bioabsorbability in the porous composite, can be preliminarily identified by measuring a whole swelling ratio of the porous composite. For example, the whole swelling ratio of the porous composite is measured. Then, a region (A) of 10% to 30% by weight from a point with the highest swelling ratio in the porous composite can be defined as a region wherein the first piece is cut out, and a region (B) of 10% to 30% by weight from a point with the lowest swelling ratio in the porous composite can be defined as a region wherein the second piece is cut out. The region other than region (A) and region (B) is defined as region (C) with a middle swelling ratio.

Further, region (A) may be a region of 10% to 30% by weight from a point with the highest swelling ratio, but preferably 0% to 20% by weight of the region having a higher swelling ratio, more preferably 0% to 30% by weight of the region having a higher swelling ratio.

In the present specification, if the swelling ratios of at least one combination of the first piece cut out of region (A) and the second piece cut out of region (B), is 1.5 times or more, a significant effect of the present invention can be obtained in the porous composite. That is to say, the effect of the present invention can be obtained, if the first and second pieces wherein the rate of swelling ratios thereof is at least 1.5 times or more, can be cut out of one porous composite. However, it is preferable that the rate of the swelling ratios is constantly 1.5 times or more in any combination of the first piece cut out of the region (A) and the second piece cut out of the region (B).

Specifically, the definition of region (A) and region (B) is performed as follows.

The porous composite is divided into, for example, four portions and they are immersed in Dulbecco's phosphate buffered saline, respectively. According to a volume of a sample, a volume of the phosphate buffered saline is adjusted. For example, about a 50-fold volume of the solution with respect to the volume of the sample, is added. The solution containing sample is incubated at 37° C. for 24 hours. The resulting sample is compared to a control sample which is not immersed, and region (A) of 10% to 30% by weight from a point with the highest swelling ratio, and region (B) of 10% to 30% by weight from a point with the lowest swelling ratio, can be determined.

Weights of the first piece and the second piece of the porous composite are not particularly limited, so long as the swelling ratio thereof may be measured, but preferably 5 to 30 mg, more preferably 5 to 20 mg, most preferably about 10 mg. Further, even if the weights of the first piece and the second piece are different from each other, the swelling ratios can be measured. However, pieces with about the same weights are preferably used. If the weights thereof are different, the difference therebetween is preferably 5 mg or less, more preferably 2 mg or less.

Figure 2:
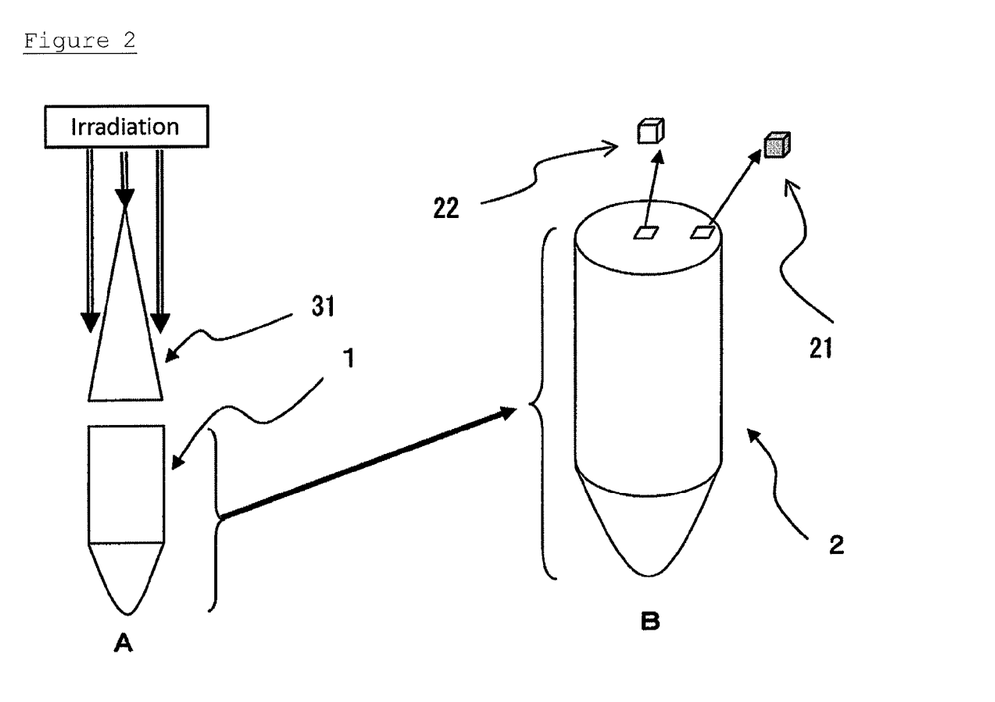
FIG. 2 is a schematic view showing an embodiment of the gradient cross-linking by the irradiation method.

Further, a shape of the first piece or the second piece is not particularly limited, so long as the swelling ratio thereof may be measured. For example, the piece with cube (regular hexahedron), cuboid, prismatic column such as a right prism, circular cylinder, or the like, may be used. For example, when the trephine for biopsy is used as described in the examples, the piece of the circular cylinder shape may be obtained. Further, as shown in FIG. 2, pieces of a part resistant to bioabsorbability (cross-linking-advanced part (21)) and a part with excellent bioabsorbability (cross-linking-non-advanced part (22)) are cut out, and the swelling ratios can be measured.

The swelling ratio of the region having an ability of rapid bone replacement, i.e. high bioabsorbability, is not particularly limited. However it is preferably 80% or more, more preferably 100% or more, most preferably 120% or more. When the swelling ratio is 80% or more by weight, the bioabsorbability thereof is excellent and the bone replacement may be rapidly induced in bone regeneration. Therefore, bone regeneration is easily promoted.

On the other hand, the swelling ratio of the region having mechanical strength is not particularly limited, but preferably 70% or less, more preferably 60% or less, most preferably 50% or less. When the swelling ratio is 70% or less, the porous composite has a sufficient mechanical strength in addition to a biological compatibility and a potential of bone replacement. Thus, the region having mechanical strength remains in a body over a long period of time, and provides a space wherein the bone tissues are regenerated therearound.

Further, the difference between the swelling ratio of the region having good bioabsorbability and biodegradation rate of the region having mechanical strength, is not particularly limited, so long as it is 1.5 times or more, but preferably 1.5 times or more, more preferably 2.0 times or more, most preferably 3.0 times or more. Furthermore, an upper limit of the difference is not particularly limited, but preferably 1000 times or less. When the difference between the swelling ratio of the region having good bioabsorbability and the swelling ratio of the region having mechanical strength is 1.5 times or more, the artificial bone satisfying the induction of bone replacement and the mechanical strength in a balanced manner is obtainable.

The density determined by the gravimetric method of the porous composite of the present invention is preferably 300 to 1500 mg/cm$^3$, more preferably 500 to 1400 mg/cm$^3$, most preferably 750 to 1200 mg/cm$^3$. When the density of the porous composite is less than 300 mg/cm$^3$, the mechanical strength thereof is insufficient. When the density of the porous composite is more than 1500 mg/cm$^3$, a degree of bone tissue entering into the porous composite becomes worse.

The density determined by the gravimetric method can be calculated as follows. The porous composite is formed into a circular cylinder or plate. Then, a weight thereof is divided by the volume measured using a vernier caliper.

The porous composite of the present invention may contain other substances. A ratio of other substances to the calcium phosphate crystal and collagen is not particularly limited, as long as the density of the porous composite is in the above density range, but the weight of the calcium phosphate crystal and collagen to the total weight of the porous composite is preferably 70% or more by weight, more preferably 75% or more by weight, most preferably 80% or more by weight. Thus, a porous composite consisting of calcium phosphate crystal and collagen is comprised in the porous composite of the present invention. The strength of the porous composite of the present invention is obtained by means of the amount of calcium phosphate crystal and cross-linking between collagen fibers. Therefore, the weight of the calcium phosphate crystal and collagen to the total weight of less than 70% by weight is not preferable. This is because the strength thereof has the possibility of reduction.

Other substances which can be contained in the porous composite include, for example, a "binder" with affinity for collagen and calcium phosphate crystal, or a medical agent for bone treatment.

As the binder, for example, there may be mentioned gelatin, glycosaminoglycan, or alginic acid. In addition, the binder includes a bioabsorbable polyester such as polylactic acid, or a functional polysaccharide such as β1-3 glucan, chitin, or chitosan.

Glycosaminoglycan (hereinafter sometimes referred to as "GAG") is a polysaccharide having a basic skeleton consisting of a repeated structure of disaccharide of hexuronic acid and hexosamine, or galactose and hexosamine. In the GAG other than a hyaluronic acid and chondroitin, the hydroxy group of the constituent sugar is partially sulfuric esterified, and the amino group of the constituent sugar is acetylated or sulfated. As the hexuronic acid, there may be mentioned, for example, glucuronic acid and iduronic acid. As the hexosamine, there may be mentioned, for example, glucosamine and galactosamine. As the GAG which can be used in the porous composite of the present invention, there may be mentioned, for example, hyaluronic acid (HA), chondroitin, chondroitin sulfuric acid (CS), heparin, heparan sulfate, keratan sulfate, Kerato sulfate, or the like. However, hyaluronic acid, which can promote an induction of angiogenesis or chondroitin sulfuric acid which widely exist in hard tissues, is preferable.

(Embodiment of Gradation of Bioabsorbability of Porous Composite)

The porous composite of the present invention has graded bioabsorbability. Thus, it can control a region wherein the bone replacement is rapidly induced by bone remodeling, and a region wherein the bone tissue is regenerated therearound by remaining in the body over a long period of time. Therefore, the porous composite can promote the regeneration of bone tissue without loss of strength in vivo.

The gradation of bioabsorbability may be continuous or discontinuous. In addition, the bioabsorbability may be continuously or discontinuously varied from one side to the other. Furthermore, the gradation of bioabsorbability may alternately exist in one porous composite. That is, a part with high bioabsorbability and a part with low bioabsorbability may be distributed in patchy fashion.

[2] Artificial Bone

The artificial bone of the present invention comprises the porous composite or consists of the porous composite. That is to say, the porous composite can be used as the artificial bone for bone regeneration in bone loss, which can satisfy bone replacement inductions and mechanical strength.

A shape of the artificial bone of the present invention is not particularly limited, and the artificial bone can be formed according to a shape of bone-deficient area.

A disorder which can be treated using the artificial bone of the present invention is not particularly limited. There may be mentioned bone tumors (chondroma, lateral curvature), artificial joint replacement and revision surgery, bone fractures, posterior cervical spinal fusion, coxarthrosis, false joints, avascular necrosis of the femoral head, and inflammation of bone marrow.

[3] Method for Preparing Porous Composite

The method for preparing the porous composite of the present invention comprises the steps of: (A) forming a porous material containing calcium phosphate and collagen, and (B) cross-linking the porous material in a gradient manner by a cross-linking treatment capable of varying cross-link density, to obtain a porous composite having at least two regions wherein the ratio of bioabsorbabilities thereof is 1.5 times or more.

<<Preparation Method Using Calcium Phosphate Crystals and Collagen Fibers>>

In one embodiment of the present invention, the porous material forming step (A) comprises the steps of: (1) crystallizing calcium phosphate, to obtain a suspension of crystals or surface modified crystals of calcium phosphate, (2) forming a collagen fibril from a soluble collagen in a collagen solution, to obtain a collagen fiber suspension, (3) mixing the collagen fibers suspension and the suspension of calcium phosphate crystals, to obtain a mixed suspension of calcium phosphate crystals and collagen fibers, and (4) forming the porous material from the mixed suspension of calcium phosphate crystals and collagen fibers. The porous composite described in item [1] can be prepared according to, but is by no means limited to, for example, the preparation method of the porous composite of the present invention.

(1) Crystallization Step

During crystallization step (1), the calcium phosphate crystal can be prepared using calcium phosphate such as $Ca(H_2PO_4)_2$, $Ca(H_2PO_4)_2 \cdot H_2O$, $CaHPO_4$, $CaHPO_4 \cdot 2H_2O$, $Ca_3(PO_4)_2$, $Ca_3(PO_4)_2 \cdot 2H_2O$, $Ca_8H_2(PO_4)_6 \cdot 5H_2O$, $Ca_3(PO_4)_2$, $Ca_{10}(PO_4)_6(OH)_2$ or the like. In particular, however, a hydroxyapatite crystal is preferable. Calcium phosphate crystals may be prepared in accordance with a conventional method such as a wet method, dry method, hydrothermal method, alkoxide method, flux growth, or the like. For example, the hydroxyapatite crystal can be prepared via the following wet method.

For example, in the case of the hydroxyapatite, calcium hydroxide (or calcium carbonate) is reacted with phosphoric acid in a solution at room temperature to about 80° C. The hydroxyapatite can be obtained by drying the resulting microcrystalline powders of hydroxyapatite. In particular, a calcium hydroxide (or calcium carbonate) solution and a phosphoric acid solution are mixed to obtain a white suspension (i.e. slurry) which is water-insoluble. As the calcium hydroxide solution, a calcium hydroxide suspension wherein calcium hydroxide is not completely dissolved, may be used. Preferably, the pH of the reaction liquid is within a range of pH 7 to 11, and the phosphoric acid solution is dropped so that a variation range of pH is 1 or less. More preferably, the reaction liquid is within a range of pH 7 to 9, and the phosphoric acid solution is dropped so that a variation range of pH is 0.5 or less. Further, the calcium phosphate crystal suspension can be obtained by calcining the resulting suspension at 50° C. to 1200° C.

In particular, 0.6 mol/L of phosphoric acid solution (for example, 2 liters) is slowly dropped into 0.5 mol/L of calcium hydroxide suspension (for example, 4 liters) until becoming pH 7.5. The resulting suspension is dried at 120° C., and then calcined at 1200° C., for 30 minutes. It can be confirmed whether or not the synthesized hydroxyapatite is single phase by measuring powder X-ray diffraction.

When the cross-linking via irradiation is carried out in the collagen fiber cross-linking step (4) mentioned below, a surface-modified calcium phosphate crystal having a vinyl group can be used. The vinyl groups, which are introduced in the calcium phosphate crystal, are cross-linked by irradiation. The introduction of the vinyl group can be carried out in accordance with a conventional method. For example, it can be performed according to the following method using trimethoxyvinylsilane.

A liquid phase is removed from a hydroxyapatite crystal suspension by centrifugation and then the solvent is replaced with ethanol. The above procedure is repeated three times to obtain a hydroxyapatite crystal suspension (6.0 mg/mL) in ethanol. Further, trimethoxyvinylsilane is added to purified water to prepare a trimethoxyvinylsilane solution of 20% by weight. The trimethoxyvinylsilane solution is added to the hydroxyapatite crystal suspension at a ratio of 9:1 (hydroxyapatite crystal suspension: trimethoxyvinylsilane solution) so as to adjust the concentration of hydroxyapatite to 6% by weight. The mixture is stirred upside down for 18 hours, and then a supernatant is removed by centrifugation. Then, the precipitate is dried at 100° C. for 2 hours in the atmosphere.

Figure 3:
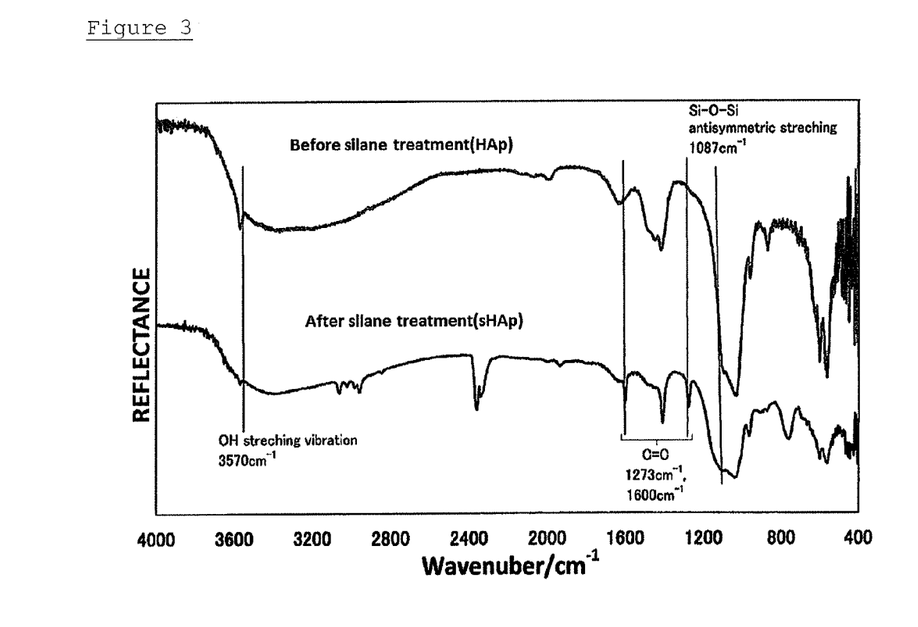
FIG. 3 is a graph showing that a trimethoxy group modified on hydroxyapatite by using trimethoxyvinylsilane, is analyzed by an infrared absorption spectrometry.
Figure 4:
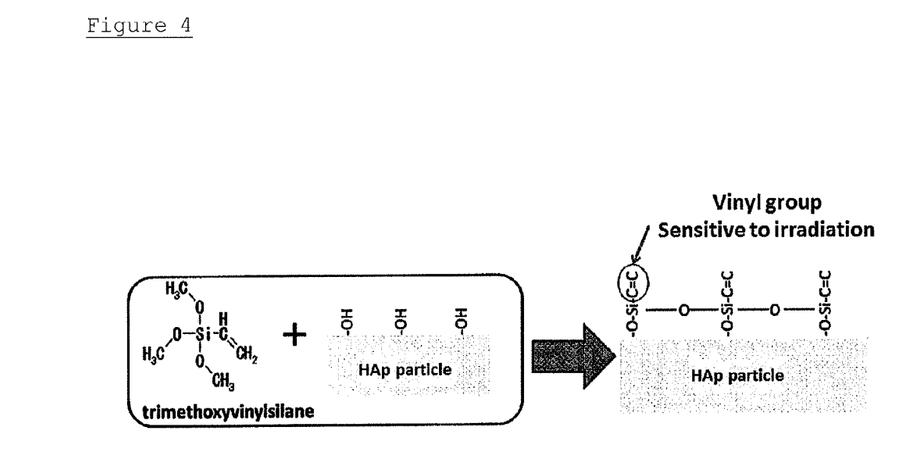
FIG. 4 is a schematic view showing the modification of a trimethoxy group on the surface of hydroxyapatite.

The introduction of a vinyl group can be confirmed by infrared absorption spectrometry. As shown in FIG. 3, comparing the sample after treatment by trimethoxyvinylsilane to one before treatment by trimethoxyvinylsilane, the OH peak of 1087 $cm^{-1}$ is decreased in the sample after treatment, and the C=C peaks of 1273 $cm^{-1}$ and 1600 $cm^{-1}$, and the Si—O—Si peak of 1087 $cm^{-1}$ are observed. Thus, it is considered that the trimethoxy group is introduced on the hydroxyapatite crystal by the reaction of the hydroxyl group of the surface of the hydroxyapatite crystal with trimethoxyvinylsilane.

Further, according to a thermogravimetry with differential thermal analysis, exothermal behaviors at 210° C. and 320° C. are observed, and thus a decrease of weight is observed at 320° C. The decrease of weight at 320° C. means that vinylsilane is covered on the surface of hydroxyapatite.

(2) Collagen Fibril Formation Step

In the collagen fibril formation step (2), a soluble collagen derived from mammal or fish is dissolved in an aqueous solvent such as water. A collagen fiber suspension can be obtained by adding a neutral buffer to an acid-soluble collagen solution. Preferably, the pH of the acid-soluble collagen solution is pH 2.0 to 6.0. The optimal pH level for collagen fibril formation varies in accordance with the type of collagen. However, many types of collagen may form the collagen fibrils at a range of pH 5 to pH 9, i.e. neutral pH, and therefore neutral buffers are frequently used for fibril formation. An appropriate ionic strength and neutral pH are important, as a condition of a neutral buffer capable of forming a collagen fibril. There is no particular limitation to the buffer, as long as it may satisfy the above condition. However, in view of a practical application, such as an artificial bone implanted in a living body, an aqueous solution containing salt, which has a buffering ability, such as a phosphate buffer, an acetate buffer, a carbonate buffer, a citrate buffer, or a Tris buffer, which has low cytotoxicity or lack cytotoxicity, is preferable. In particular, a phosphate buffer (such as sodium phosphate buffer) is preferable because it is an inexpensive, neutral buffer that does not exhibit toxicity to a living body, and has an excellent collagen fibril formation ability compared with other neutral buffers.

In the collagen fibril formation step, collagen fiber in the collagen fiber suspension may be concentrated by centrifugation or pressure dehydration to obtain a concentrated collagen fiber suspension.

In the centrifugation of the collagen fiber suspension, the centrifugation by a centrifuge and the homogenization can be repeated one to ten times. In particular, the centrifugation is not particularly limited, as long as water may be removed from the collagen fiber, but a centrifugal force is preferably 2000 g to 20000 g. For example, the centrifugation can be carried out at 10000 rpm, using the centrifuge GRX-220 (TOMY DIGITAL BIOLOGY CO., LTD.). The collagen fiber suspension is centrifuged by the centrifuge, to separate collagen fiber from water, and subsequently, water is removed to obtain a pasty collagen fiber. Then, the pasty collagen fiber is homogenized using a homogenizer in order to easily isolate water maintained between collagen fibers. Further, after homogenizing, the collagen fiber suspension is repeatedly centrifuged using the centrifuge to remove the isolated water. As for the homogenizer, a conventional one may be used. For example, the collagen fiber suspension may be homogenized at 5000 rpm using CELLMASTER (AS ONE). The number of centrifugations is not limited, but 1 to 10 times, preferably 1 to 8 times, more preferably 1 to 5 times, most preferably 1 to 3 times, in view of an efficiency.

In the case of the concentration by the pressure dehydration, the collagen fiber suspension may be concentrated by single pressure dehydration. However, the repetition of the pressure dehydration and homogenization can be repeated 1 to 10 times. A concentration of collagen fibers in the collagen fiber suspension is about 0.4 to 0.5% by weight, but a collagen fiber suspension of 10% or more by weight can be obtained by centrifugation and pressure dehydration.

(3) Mixing Step

In the mixing step (2), the mixed suspension of calcium phosphate crystals and collagen fibers can be obtained by mixing the collagen fiber suspension (including concentrated collagen fiber suspension) with the calcium phosphate crystal suspension. The calcium phosphate crystal suspension to be mixed with the collagen fiber suspension is not particularly limited, but preferably hydroxyapatite crystal suspension.

Further, preferably the resulting mixture is sufficiently stirred and then defoamed using a swing type centrifuge. This is so a commingling of air bubbles with the mixture can be prevented before freeze-drying.

(4) Porous Material Forming Step

In the porous material forming step (4), the porous material is formed from the mixed suspension of calcium phosphate crystals and collagen fibers. As the method for forming the porous material, known methods may be used. In particular, there may be mentioned a freeze-drying method. In the case that the freeze-drying method is used as the method for forming the porous material, a forming container with a desired size and shape is prepared, and then the mixed suspension of calcium phosphate crystals and collagen fibers is poured thereinto. A material of the forming container is not particularly limited, as long as it can be used through freezing in a refrigerating machine and depressurization in a freeze dryer. For example, it is possible that the forming container with an arbitrary size and shape is manufactured using silicon rubber. The mixed suspension of calcium phosphate crystals and collagen fibers in the forming container is freezed in the refrigerating machine at, for example, $-80°$ C. to $-0°$ C. The freezed, mixed suspension of calcium phosphate crystals and collagen fibers is placed in the freeze dryer and then freeze-dried at, for example, $-30°$ C. to $-40°$ C. of a shelf temperature until moisture has evaporated.

In the porous material forming step, the collagen fibers in the porous material may be cross-linked by thermal dehydration, in order to obtain a certain mechanical strength or more. For example, the thermal cross-linking can be carried out by heat-treating the porous material at $130°$ C. for 24 hours under reduced pressure.

<<Preparation Method Using Calcium Phosphate-Collagen Composite Fiber>>

In the porous material forming step (A) of the other embodiment of the present invention, a calcium phosphate-collagen composite fiber and a buffer are mixed and gelated, to form a porous material. This step is described in a method for preparing porous material in Japanese Unexamined Patent Publication (Kokai) No. 2007-98118. In this embodiment, the calcium phosphate is not particularly limited, but preferably hydroxyapatite.

In particular, the hydroxyapatite-collagen composite fiber may be mixed with the buffer, and then the mixture may be freeze-dried. However, the freeze-drying can be carried out after the following gradient cross-linking step (B). Further, the hydroxyapatite-collagen composite fiber may be mixed with the buffer, and then incubated. A c-axis of the hydroxyapatite-collagen composite fiber is preferably oriented in a fiber axis direction.

The hydroxyapatite-collagen composite fiber is mixed with the buffer, and then the c-axis of the hydroxyapatite is oriented in the fiber axis direction. Whereby, the porous material has a sponge-like elasticity, and can solve conventional problems related to mechanical strength and a poor handling in clinical practice.

The buffer used in the present invention is one controlling ionic species and ionic strength. For example, various buffers such as a phosphate buffer and so on wherein the ionic species is an inorganic ion, or a Tris buffer, an acetate buffer, and so on wherein the ionic species is an organic ion, can be used. Further, the ionic strength of the buffer is preferably 0.01 to 0.5 mol/L, more preferably 0.02-0.2 mol/L, as a corresponding value in a pasty hydroxyapatite-collagen composite.

For example, the porous material may be prepared as follows.

(1) 1 g of the hydroxyapatite-collagen composite fiber mixture (mixture ratio of HAp/Col is 80/20) and 8 mL of phosphate buffer (0.1 mol/L, pH6.8) are stirred and combined evenly, and incubated to gelate.

(2) The gel-like mixture is poured into a container (such as a polystyrene dish for cell culture and a 24 well-plate for cell culture) which is appropriately selected.

The resulting porous material can be used in the following gradient cross-linking step.

(B) Gradient Cross-Linking Step

There is no particular limitation to the cross-linking method in the gradient cross-linking step, so long as the porous composite wherein a first piece and a second piece can be cut out thereof and the ratio of bioabsorbabilities thereof is 1.5 times or more, can be prepared. For example, there may be mentioned a wet type cross-linking method using an aldehyde based, isocyanate based, or carbodiimide based cross-linking agent, or tannin; a cross-linking method using a metallic ion such as chromium ion or ferric iron; a cross-linking method via ultraviolet irradiation; a thermal cross-linking method; a glutaraldehyde vapor deposition method; or a cross-linking method via irradiation. However, the glutaraldehyde vapor deposition method or the cross-linking method via irradiation is preferable. In this step, a cross-linking treatment capable of varying cross-link density can be carried out using the above cross-linking method.

(Glutaraldehyde Vapor Deposition Method)

When the glutaraldehyde vapor deposition method is used in the gradient cross-linking step, a degree of cross-linking of the porous material may be controlled by regulating volatilization and diffusion of glutaraldehyde into the porous material, to thereby prepare regions having graded bioabsorbabilities in the porous material.

The glutaraldehyde vapor deposition method may be carried out according to a conventional method. Specifically, glutaraldehyde is diluted with purified water, to prepare a glutaraldehyde solution of about 1% to 25% by volume. In the chemical cross-linking using the glutaraldehyde vapor, a concentration of glutaraldehyde has an effect on the diffusion thereof. If the concentration of glutaraldehyde is high, a rate of diffusion is fast. If the concentration of glutaraldehyde is low, a rate of diffusion is slow. Thus, the rate of diffusion of glutaraldehyde can be controlled by adjusting the concentration thereof.

The glutaraldehyde solution is poured into an upper-open type container (such as glass bottle or petri dish). The glutaraldehyde solution and the sample to be cross-linked are placed in a desiccator and so on, and the cross-linking reaction is performed at $37°$ C. for about 1 to 24 hours.

In the cross-linking by the glutaraldehyde vapor deposition method, glutaraldehyde diffuses through a surface thereof into an inside thereof, and then amino groups are cross-linked with one another, or the amino group and SH group are cross-linked. Therefore, in the gradient cross-linking step, the porous material may be cross-linked in a gradient manner by preventing the diffusion of glutaraldehyde from a surface of a side wherein a weak cross-linking is introduced. In particular, it is possible to introduce the gradient cross-linking by covering the surface wherein the diffusion of glutaraldehyde is suppressed, using a film.

The film is not particularly limited, as long as it can prevent or suppress a permeation of glutaraldehyde. Examples of the film include a silicone film, a polyvinyl chloride film, a polypropylene film, a polymethylmethacrylate film, a polytetrafluoroethylene film, or a polystyrene film. In particular, the polystyrene film is preferable.

(Cross-Linking Method Via Irradiation)

When the cross-linking method via irradiation is used in the gradient cross-linking step, it is possible to introduce the gradient cross-linking by variations of the collagen concentrations in the porous composite under a wet condition. This is because collagen fibers are cross-linked with one another through irradiation in a wet condition.

The porous composite having some regions with different bioabsorbabilities can be prepared using the porous material with different collagen concentrations as follows.

The porous materials having different ratios of the collagen to apatite are prepared. Then, the porous materials are layered, to thereby obtain a layered porous material having regions with different collagen concentrations. The porous composite having at least two regions wherein the ratio of bioabsorbabilities thereof is 1.5 times or more can be obtained by irradiating the layered porous material.

When the cross-linking method via irradiation is used in the gradient cross-linking step, the gradient cross-linking can be introduced by varying an introduction of a functional group sensitive to radiation on calcium phosphate. Further, even when the amounts of the functional group are not varied, the gradient cross-linking can be introduced by controlling the amount of irradiation. The introduction of the functional group sensitive to radiation, i.e. the vinyl group into calcium phosphate can be carried out according to the method described in the "crystallization step (1)".

For example, the porous composite having some regions with different bioabsorbabilities can be prepared by controlling the introduction of a vinyl group as follows.

A number of calcium phosphate crystal suspensions having different introduction amounts of a vinyl group are prepared. The resulting calcium phosphate crystal suspensions are mixed with collagen suspensions respectively to prepare a number of porous materials having different introduction amounts of a vinyl group. The porous materials are layered to obtain a layered porous material having regions with different introduction amounts of the vinyl group. The porous composite having at least two regions wherein the ratio of bioabsorbabilities thereof is 1.5 times or more can be obtained by irradiating the layered porous material.

Further, the gradient cross-linking can be introduced by controlling the amount of radiation. For example, the introduction of the gradient cross-linking can be performed as follows.

The method for controlling the amount of radiation to the porous material is not particularly limited. For example, the amount of radiation can be controlled using a tapered lead plate. As shown in FIG. 2, the tapered circular cone is used. That is, the radiation is sent to the porous material from above through a circular cone. According to the above irradiation, a center region of the circular cone is thick, and thus a center of the porous material is resistant to cross-linking via irradiation due to low-dose radiation. Therefore, the center of the porous material has excellent bioabsorbability and swelling properties, but has a weak mechanical strength. In contrast, a peripheral region of the circular cone is thin, and thus the surrounding of the porous material is sensitive to cross-linking via irradiation due to high-dose radiation. Therefore, the surrounding of the porous material is resistant to bioabsorbability, and has an excellent mechanical strength.

A radiation source is not particularly limited, but a gamma ray, an electron ray, or a beta ray can be used. However, the gamma ray is preferable.

In the cross-linking via irradiation under wet conditions, the cross-linking is introduced between collagens, or between collagen and apatite at the interface. Thus the steric distance therebetween is important. That is, the porous material having higher density can be rigidly cross-linked. Further, the cross-linking via irradiation is characterized in that the material permeability of irradiation is excellent, the cross-linking occurs evenly in molecules, the cross-link density is easily controlled, and the cross-linking can be performed regardless of the shape of the material.

The porous composite may be cross-linked via irradiation under wet conditions or dry conditions. However, the wet conditions are preferable. When the cross-linking is carried out under wet conditions, the peptide bond in a collagen molecule is not broken and thus the collagen molecule is not degraded. Therefore, the collagens can be effectively cross-linked with each other. A moisture content of the porous material is not particularly limited, but is preferably the same volume as one of the porous materials, or 1 to 10 times the volume thereof. Further, the cross-linked via irradiation can be carried out through a gas replacing an inactive gas such as nitrogen or argon.

EXAMPLES

The present invention now will be further illustrated by, but is by no means limited to, the following Examples.

Example 1

Example 1

In this example, the porous composite with gradient bioabsorbability was manufactured by the glutaraldehyde vapor deposition method.

(i) Preparation of the Hydroxyapatite Crystal Suspension

The hydroxyapatite crystal is synthesized through the wet method. 0.6 mol/L of phosphoric acid solution (2 litters) was slowly dropped into 0.5 mol/L of calcium hydroxide suspension (4 litters) until becoming pH7.5. The resulting suspension was dried at 120° C., and then calcined at 1200° C., for 30 minutes using an electrical furnace. It was confirmed that the synthesized hydroxyapatite was single phase by measuring powder X-ray diffraction.

(ii) Preparation of the Collagen Fiber Suspension

A tilapia scale collagen was dissolved to a concentration of 1% by weight of tilapia scale collagen with hydrochloric acid solution (pH4.0). A buffer (PB) was prepared by mixing 0.1 mol/L of sodium hydrogenphosphate solution with 0.1 mol/L of monobasic sodium phosphate so that the pH was pH8.2. The collagen solution and the PB were mixed in equal amount, and then the mixture was allowed to stand at 27° C. for 3 days, to prepare a collagen fiber gel. The fiber gel was concentrated by centrifuging the same and removing a supernatant. The concentrated collagen fiber gel was dried at 130° C. with the collagen concentration measured thereafter. The collagen concentration was 17.3% by weight.

(iii) Preparation of Dried Composite

The collagen concentration of the collagen fiber gel obtained in the step (ii) was adjusted to 10% by weight, and then the hydroxyapatite crystal was mixed therewith so that the weight ratio of the collagen and the hydroxyapatite crystal was 4:6. They were sufficiently mixed and stirred using the Cellmaster. The resulting composite gel (hydroxyapatite crystal-collagen fiber mixed suspension) was charged to a 25 mL centrifuge tube, and then defoamed by centrifuging at 1000 G for 5 minutes using the swing-type centrifuge. The resulting composite was poured into a container (10 mm×10 mm×10 mm) and frozen at −20° C. for 1 day. Further, the composite was freeze-dried for 48 hours. Then, the composite was thermally cross-linked by heating at 130° C. for 24 hours under a reduced-pressure atmosphere. The resulting composite was referred to as sample A.

(iv) Gradient Cross-Linking by the Glutaraldehyde Vapor Deposition Method

The cross-linking via glutaraldehyde (GA) gas was carried out as follows. The glutaraldehyde was diluted with purified water to prepare a glutaraldehyde solution of 10% by volume. 20 mL of GA solution was poured into a petri dish and allowed to stand in a desiccator together with the prepared sample (sample A; 10 mm×10 mm×10 mm). The desiccator pressure was reduced and then the desiccator was placed in an incubator and a cross-linking reaction was performed at 37° C., for 1, 6, 12, or 24 hours. Five surfaces of sample A were covered by polystyrene films, GA gas diffuses through one surface only into an inside thereof, and the cross-linking reaction was carried out (FIG. 1A). The resulting porous composite was referred to as sample A-GA.

The gradient cross-linking via GA can be confirmed on the basis of a visual evaluation. In particular, the sample treated by GA for 3 hours was cut in the center thereof by a scalpel, and observed. A color of the sample was varied from yellow to white in order of distance from a GA gas-diffused surface. It was considered that the GA gas diffused surface was cross-linked to a higher degree. Further, in the sample treated by GA for 3 hours, a contrast of the colors of the sample was able to be confirmed more explicitly.

Example 2

In this example, the porous composite swelled was manufactured by irradiation.

(i) Preparation of Hydroxyapatite Crystal Suspension and Introduction of Vinyl Group Thereto The hydroxyapatite crystal is synthesized through the wet method. 0.6 mol/L of phosphoric acid solution (2 litters) was slowly dropped into 0.5 mol/L of a calcium hydroxide suspension (4 liters) until it reached pH7.5. The resulting suspension was dried at 120° C., and then calcined at 1200° C., for 30 minutes using an electrical furnace. It was confirmed that the synthesized hydroxyapatite was single phase by measuring powder X-ray diffraction.

The introduction of the vinyl group was performed as follows.

The hydroxyapatite suspension was centrifuged so that a precipitate was separated from a liquid, and then ethanol was added to the precipitate. The hydroxyapatite suspension (60 mg/mL) was prepared by repeating the above procedure. On the other hand, trimethoxyvinylsilane was added to purified water, to prepare trimethoxyvinylsilane (20% by weight). The trimethoxyvinylsilane solution was added to the hydroxyapatite crystal suspension at a ratio of 9:1 (hydroxyapatite crystal suspension:trimethoxyvinylsilane solution) so as to adjust the concentration of hydroxyapatite to 6% by weight. The mixture was stirred upside down for 18 hours, and then a supernatant was removed by centrifugation. Then, the precipitate was dried at 100° C. for 2 hours in the atmosphere. Vibrations derived from Si—O and from the vinyl group were both confirmed by the infrared absorption spectrometry. Further, the exothermal behaviors at 210° C. and 320° C. and the decrease of weight at 320° C. were observed from the results of the differential thermal analysis. These results indicate that, according to the present method, the silane agent can modify the surface of the hydroxyapatite.

(ii) Preparation of Collagen Fiber Suspension

The procedures of Example 1(ii) were repeated to obtain the collagen fiber suspension.

(iii) Preparation of Porous Composite Swelled

The hydroxyapatite crystal was mixed with the resulting collagen fiber suspension so that the weight ratio of the collagen and the hydroxyapatite crystal was 4:6. They were sufficiently mixed and stirred using the Cellmaster. The resulting composite gel (hydroxyapatite crystal-collagen fiber mixed suspension) was charged to a 25 mL centrifuge tube, and then defoamed by centrifuging at 1000 G for 5 minutes using the swing type centrifuge. The resulting wet type composite was referred to as sample C.

(iv) Gradient Cross-Linking Via Irradiation

In order to gradually cross-link via irradiation, irradiation was performed using a tapered circular cone (height is 10 cm, and diameter is 1 cm) made of lead. As shown in FIG. 1, the lead-tapered circular cone was applied on the top of sample C charged in the centrifuge tube, and then 5.3 kGy/h of gamma rays were irradiated using cobalt 60 as a radiation source (FIG. 2A). The irradiation time is about 10 hours. After irradiation, the composite was frozen at −20° C. for 1 day, and further freeze-dried for 48 hours. Then, the composite was thermally cross-linked by heating at 130° C. for 24 hours under a reduced-pressure atmosphere. The resulting composite was referred to as sample C-g.

Example 3

(i) Preparation of Hydroxyapatite-Collagen Composite Fiber 200 mL of collagen solution wherein 2.0 g of tilapia scale collagen was dissolved in a phosphoric acid solution (0.15 mol/L), and 200 mL of 0.5 mol/L of a calcium hydroxide suspension (0.25 mol/L) were prepared. 200 mL of purified water were charged to a 1000 mL volume of a beaker. The prepared collagen solution and calcium hydroxide suspension were simultaneously added to the purified water of 25° C., at 4 mL/min of drip rate, so that the pH was pH8.0±0.5. After dropping, a supernatant was removed by suction filtration. The resulting hydroxyapatite-collagen composite fiber was frozen at −20° C., and then freeze-dried. According to the results of the differential thermal analysis (TG-DTA) of the freeze-dried composite fiber, the weight ratio of the hydroxyapatite and the collagen was 8:2.

(ii) Preparation of Hydroxyapatite-Collagen Composite Fiber Gel and Forming Thereof 4 mL of phosphate-buffered saline (0.1 mol/L, pH8.0; mixed buffer of monobasic sodium phosphate solution and sodium hydrogenphosphate solution) were added to 2 g of the prepared hydroxyapatite/collagen composite fiber. The mixture was sufficiently kneaded to obtain an evenly-mixed hydroxyapatite-collagen composite fiber gel. The mixture was charged to a cell culture dish having a diameter of 35 mm and a height of 10 mm (Easy-Grip Dish, Falcon), so that a height thereof was 3 mm.

(iii) Gradient Cross-Linking Via Irradiation

In order to gradually cross-link via irradiation, irradiation was performed using a circular cone (height is 4 cm, and diameter is 35 mm) made of lead. The composite fiber was placed on cobalt 60 as a radiation source, and then the composite fiber was irradiated. After irradiation, the composite fiber was frozen at −20° C., and then freeze-dried for 48 hours. Further, the composite was thermally cross-linked by heating at 130° C. for 12 hours under a reduced-pressure atmosphere.

(iv) Measurement of Mechanical Strength Gradient by the Indentation Test

The resulting hydroxyapatite-collagen composite fiber porous material was immersed in Dulbecco's phosphate-buffered saline, and was subjected to an indentation test using a texture analyzer (TA-XTplus). As a cylinder, cylindrical probe with a diameter of 2 mm (P/2) was used. There were five points between an edge of the sample and the center of the sample. As a result, a difference of strength ratio of about 2 times at a distortion rate of 30% is observed between the edge with a high irradiation and the center with low irradiation.

Comparative Example 1

The procedure of Example 2 was repeated, except that the introduction of the vinyl group was not performed in the step (i) of Example 2, to obtain sample D as the composite in the step (iii), and sample D-g as the porous composite in the step (iv).

Reference Example 1

In this Reference Example 1, the swelled, porous composite was manufactured by a cross-linking via irradiation without gradient. The procedures of steps (i), (ii), and (iii) of Example 2 were repeated to obtain sample C.
(iv) Cross-Linking Via Irradiation Sample C in a centrifuge tube was irradiated with 50 KGy of gamma rays, using cobalt 60 as a radiation source. After irradiation, the composite was frozen at −20° C. for 1 day, and further freeze-dried for 48 hours. Then, the composite was thermally cross-linked by heating at 130° C. for 24 hours under a reduced-pressure atmosphere. The resulting porous composite was referred to as sample C-γ.

Comparative Example 2

In this Comparative Example 1, sample D without introduction of the vinyl group was cross-linked by the irradiation without gradient to manufacture the swelled porous composite. The procedures of steps (i), (ii), and (iii) of Comparative Example 1 were repeated to obtain sample D.
(iv) Cross-Linking Via Irradiation Sample D in a centrifuge tube was irradiated with 50 KGy of gamma rays, using cobalt 60 as a radiation source. After irradiation, the composite was frozen at −20° C. for 1 day, and further freeze-dried for 48 hours. Then, the composite was thermally cross-linked by heating at 130° C. for 24 hours under a reduced-pressure atmosphere. The resulting porous composite was referred to as sample D-γ.

Reference Example 2

In this Reference Example 2, a dried, porous composite was manufactured by a cross-linking via irradiation without gradient. The steps (i) and (ii) of Example 2 were repeated in order to obtain a hydroxyapatite crystal suspension and a collagen fiber suspension.
(iii) Preparation of Dried, Porous Composite The hydroxyapatite crystal suspension was mixed with the collagen fiber suspension so that the weight ratio of the collagen and the hydroxyapatite crystal was 4:6. They were sufficiently mixed and stirred using the Cell master. The resulting composite gel (hydroxyapatite crystal-collagen fiber mixed suspension) was charged to a 25 mL centrifuge tube, and then defoamed by centrifuging at 1000 G for 5 minutes using the swing type centrifuge. The resulting composite was frozen at −20° C. for 1 day, and further freeze-dried for 48 hours. The composite was thermally cross-linked by heating at 130° C. for 24 hours under a reduced-pressure atmosphere. The resulting dried composite was referred to as sample A.
(iv) Cross-Linking Via Irradiation The resulting dried composite A was put in a sterilized bag, and oxygen in the bag was adsorbed on a deoxidant. Then, the dried composite was irradiated with 50 KGy of gamma rays, using cobalt 60 as a radiation source. The resulting porous composite was referred to as sample A-γ.

Comparative Example 3

In this Comparative Example 3, the sample without introduction of a vinyl group was cross-linked by the irradiation without gradient to manufacture the dried, porous composite. The procedures of steps (i) and (ii) of Comparative Example 1 were repeated to obtain a hydroxyapatite crystal suspension and a collagen fiber suspension.
(iii) Preparation of Dried, Porous Composite The hydroxyapatite crystal suspension was mixed with the collagen fiber suspension so that the weight ratio of the collagen and the hydroxyapatite crystal was 4:6. They were sufficiently mixed and stirred using the Cell master. The resulting composite gel (hydroxyapatite crystal-collagen fiber mixed suspension) was charged to a 25 mL centrifuge tube, and then defoamed by centrifuging at 1000 G for 5 minutes using the swing type centrifuge. The resulting composite was frozen at −20° C. for 1 day, and further freeze-dried for 48 hours. The composite was thermally cross-linked by heating at 130° C. for 24 hours under a reduced-pressure atmosphere. The resulting dried composite was referred to as sample B.
(iv) Cross-Linking Via Irradiation The resulting dried composite B was put in a sterilized bag, and oxygen in the bag was adsorbed on a deoxidant. Then, the dried composite B was irradiated with 50 KGy of gamma rays, using cobalt 60 as a radiation source. The resulting porous composite was referred to as sample B-γ.

<<Determination of Region (A) and Region (B) Using the Biodegradation Rate Determined by Collagenase Digestion>>

The region containing the first piece having higher bioabsorbability, and the region containing the second piece having lower bioabsorbability in the porous composite were determined by a collagenase biodegradation test.

A Dulbecco's phosphate-buffered saline (pH7.2) containing collagenase of 2.0 units (0.01 mg)/mL, or 200 units (1 mg)/mL is prepared. 30 mL of the Dulbecco's phosphate-buffered saline were added to 0.3 g of the porous composite (sample A-GA) obtained in Example 1. The solution containing the sample is placed in a bioshaker, and the sample was reacted at 37° C. for 1, 3, 12, 18 or 24 hours while shaking at 50 rpm. After reacting, the sample was collected and washed by distilled water for 1 hour. The sample was frozen in a deep freezer at −20° C., and then freeze-dried. A dry weight of the resulting sample was measured and a biodegradation rate was calculated according the equation (I).

$$\text{Biodegradation rate} = (W_0 - W_t)/W_0 \times 100 \tag{I}$$

The samples reacted with GA gas for 12, 18, or 24 hours cannot be degraded even in a solution containing 1 mg/mL of collagenase because GA gas diffuses into the whole thereof. In the case of the collagenase (0.01 mg/mL) degradation test of the sample reacted with GA gas for 3 hours, the sample was degraded in order, from an opposite surface of a GA gas-diffused surface. According to time-series weight change by the biodegradation rate calculated using the equation (I), the biodegradation rate of the sample reacted for 1 hour was about 30%, the biodegradation rate of the sample reacted for 24 hours was about 70%, and the biodegradation rate of the sample reacted for 24 hours was about 100%. Therefore, the biodegradation rate of the above sample can be divided into largely three according to the time series. Further, in the case of the collagenase (0.01 mg/mL) biodegradation test of the sample reacted with GA gas for 6 hours, the sample was degraded in order, from an opposite surface of a GA gas-diffused surface. According to the time-series weight change by the biodegradation rate calculated using the equation (I), the biodegradation rate of the sample reacted for 1 hour was about 20%, the biodegradation rate of the sample reacted for 12 hours was about 40%, and the biodegradation rate of the sample reacted for 24 hours was about 60%. Therefore, the biodegradation rate of the above sample can be divided into largely three according to the time series.

That is to say, it was possible to determine 30% by weight of a region having a higher biodegradation rate, and 30% by weight of a region having a lower biodegradation rate in the sample reacted with GA gas for 3 hours.

<<Collagenase Biodegradation Test>>

10 mg of a piece in 30% by weight of a cross-linking-advanced region having a lower biodegradation rate, and 10 mg of a piece in the 30% by weight of a cross-linking-non-advanced region having a higher biodegradation rate were cut out of sample A-GA reacted for 6 hours, using a trephine for biopsy (FIG. 1B). Each of the samples (A-GA) was immersed in a Dulbecco's phosphate-buffered saline (pH7.2) containing collagenase of 2.0 units (0.01 mg)/mL, or 200 units (1 mg)/mL. 3 mL of the above collagenase solution was added to each of the pieces in a multi well plate, and each of the pieces was reacted therewith for a predetermined time, while shaking at 50 rpm. After the reaction, each sample was collected and washed by distilled water for 1 hour. The sample was freeze-dried under the same condition as the step (iii) in the preparation of the dried, porous composite, and then a biodegradation rate was calculated according to the equation (I).

In the sample treated with collagenase for 6 hours, a biodegradation rate of the piece in the cross-linking-advanced region was about 10%, and a biodegradation rate of the piece in the cross-linking-non-advanced region was about 90%. Therefore, the ratio of the second piece to the first piece was 9.0.

<<Determination of Region (A) and Region (B) Using the Swelling Ratio>>

The region containing the first piece having higher bioabsorbability, and the region containing the second piece having lower bioabsorbability in the porous composite were determined by measuring the swelling ratio.

The porous composite, sample C-g, obtained in Example 2 was divided into four pieces. 300 mL of Dulbecco's phosphate-buffered saline was added to the divided porous composite of 0.3 g, and the porous composite was subsequently immersed. The solution containing the sample was allowed to stand at 37° C. for 24 hours. 10 to 30% by weight of the region having a higher swelling ratio, and 10 to 30% by weight of the region having a lower swelling ratio were determined by comparing the resulting samples and samples which were divided and not immersed.

<<Swelling Ratio>>

10 mg of the piece in 30% by weight of region (A) having a higher swelling ratio, and 10 mg of the piece in the 30% by weight of the region having a lower swelling ratio were cut out of the sample C-g obtained in Example 2, according to the method shown in FIG. 1B. The sample was placed in a container with 5 mL of purified water for 24 hours at room temperature. In order to remove excess fluid, the sample was allowed to stand on filter paper for 1 minute. Then, the wet weight thereof was measured, and the swelling ratio was calculated according to the equation (III)

The swelling ratio of the piece which had received high amounts of gamma rays was about 20%, but the swelling ratio of the piece which had received low amounts of gamma rays was about 40%. Thus, the ratio of the swelling ratio of the second piece to the swelling ratio of the first piece was 2.0.

Reference Experimental Example 1

In this Experimental Example, it was confirmed that the compressive strength of the porous composite was increased by the cross-linking via irradiation.

Four samples (φ10 mm×10 mm), i.e. the samples A and A-γ obtained in Reference Example 2 and the sample B and B-γ obtained in comparative Example 3, were subjected to a compression test, so that the mechanical characteristics thereof were measured. In order to confirm an effect of the cross-linking via irradiation, the samples were immersed in Dulbecco's phosphate-buffered saline for 3 hours, and subsequently, the compressive strength of the samples were measured at 0.1 mm/min of crosshead speed using 50 kg of a load cell. In the hydroxyapatite-collagen, collagen molecules or collagen fibers were fragmented by the gamma ray irradiation, and further the collagen cannot maintain a skeletal structure thereof by an entry of water. In sample A-γ using a vinylsilane surface-modified hydroxyapatite crystal, the compressive strength thereof was remarkably increased by the cross-linking via irradiation, in contrast. Therefore, it is considered that the cross-linking was formed at an interface between the collagen and the hydroxyapatite crystal by gamma ray irradiation, and therefore the fragmentation of collagen molecules which forms the skeletal structure, was decreased, even if the sample was immersed in Dulbecco's phosphate-buffered saline.

TABLE 1

| γ-lay irradiation | Sample | Stress at 20% distortion rate (kPa) |
|---|---|---|
| No | B(HAp/Col) | 13.5 |
|  | A(s-HAp/Col) | 14.56 |
| Yes | B-γ(HAp/Col) | 4.46 |
|  | B-γ(s-HAp/Col) | 26.84 |

Reference Experimental Example 2

Samples C and C-g obtained in Example 2, and samples D and D-g were subjected to a compression test, according to the method described in Reference Experimental Example 1.

As a result, the strength of the sample with gradient was apparently weak, compared to that of the sample without gradient (C and D). Further, the sample with gradient had two times or more strength, compared to that of the dried sample. Furthermore, when the swelling ratio of the sample immersed in Dulbecco's phosphate-buffered saline for 3 hours was confirmed on the basis of a visual evaluation, the swelling in the center thereof was observed. Accordingly, it became apparent that some regions having various swelling ratios were formed in an inside of material by gamma ray irradiation using the circular cone made of lead.

Reference Example 3

Figure 5:
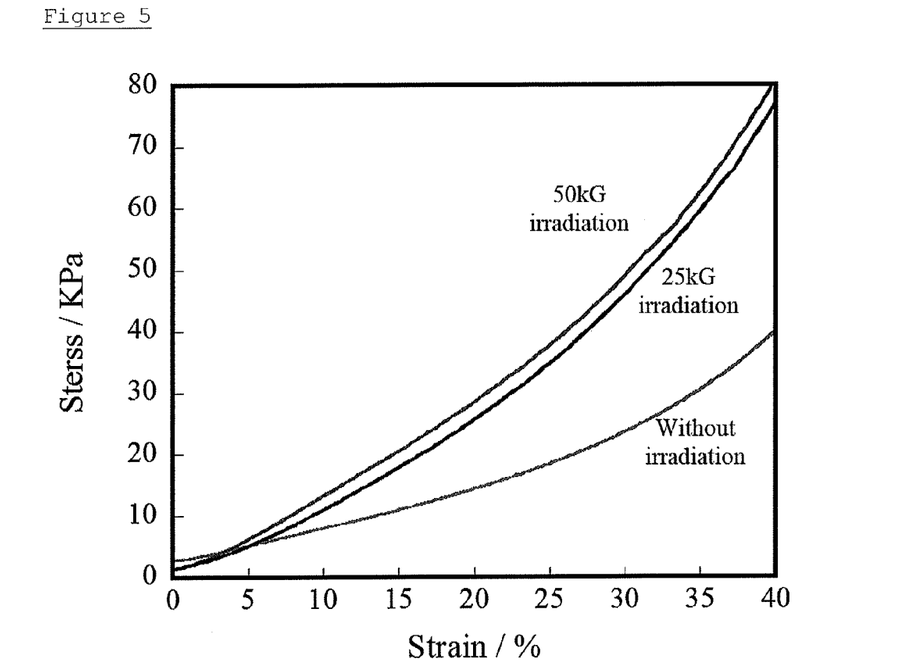
FIG. 5 is a graph showing an increased compressive strength of porous composite by the gamma irradiation under wet conditions.
Figure 6:
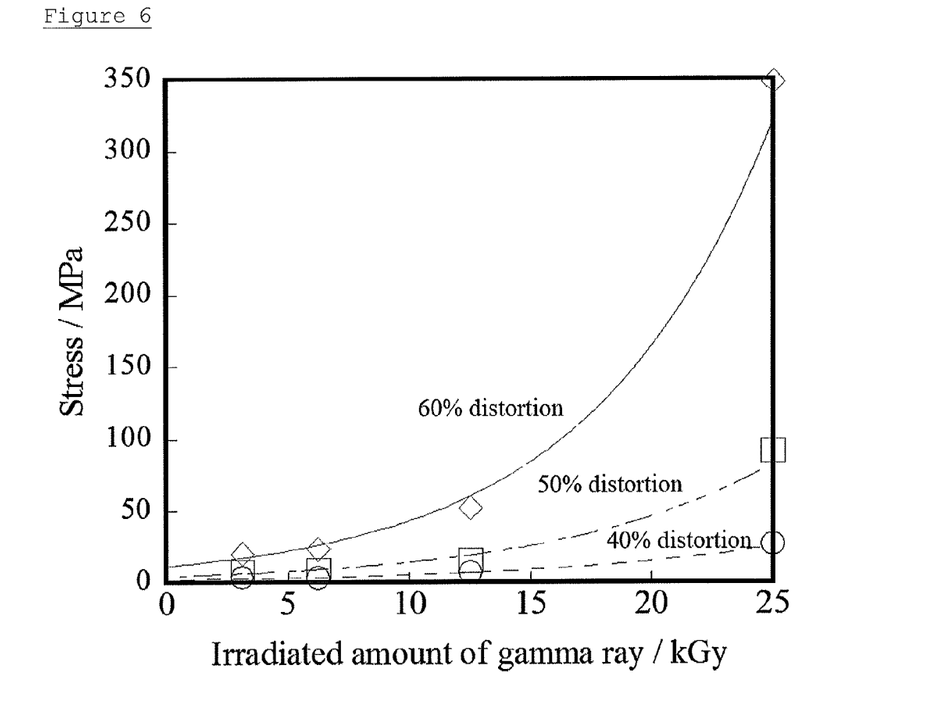
FIG. 6 is a graph showing that the compressive strengths at 40%, 50%, and 60% distortion rates are significantly increased by increasing an amount of gamma irradiation under wet conditions.

In this reference example, it was confirmed that the cross-linking with gradient can be carried out by the gamma ray irradiation under wet conditions.
(i) Vinylsilane Modification of Hydroxyapatite Nano Crystal A hydroxyapatite nano crystal was suspended to 100 mL of 90% ethanol solution, so as to adjust the concentration of the hydroxyapatite nano crystal to 6% by weight. Then, 100 mg of a vinylsilane coupling agent was mixed with the suspension. After sufficiently suspending and rotating for 18 hours, a supernatant was removed by centrifugation. Further, the precipitate was washed by 90% ethanol through centrifugation. Then, the precipitate was dried at 100° C. for 2 hours, to prepare the vinylsilane-modified hydroxyapatite.
(ii) Enhancement of Compressive Strength by γ-Lay Irradiation The resulting vinylsilane-modified hydroxyapatite and a concentrated collagen (10% by weight) were evenly suspended so that the weight ratio of the vinylsilane-modified hydroxyapatite to collagen was 60/40. The suspension was irradiated with gamma-rays at 25 kGy or 50 kGy under wet conditions. Subsequently, the suspension was frozen at −20° C. and freeze-dried. The resulting material was immersed in Dulbecco's phosphate-buffered saline at room temperature for 4 hours and then subjected to a compression test. As a control, a sample which was frozen and freeze-dried without gamma ray irradiation was used. The results were shown in FIG. 6. The distortion rate was plotted on an abscissa axis and the stress was plotted on a longitudinal axis, to obtain an S-S curve. As is obvious from FIG. 5, the compressive strength of the material with gamma ray irradiation was increased two times or more, compared to that of the material without gamma ray irradiation.

Further, the compressive strengths of the materials with gamma ray irradiation of 25 kGy and 50 kGy were about the same. Therefore, it was considered that gamma ray irradiation of 25 kGy is a maximal required amount.

The vinylsilane-modified hydroxyapatite and the concentrated collagen (8% by weight) were evenly suspended so that the weight ratio of the vinylsilane-modified hydroxyapatite to collagen was 60/40. The suspension was irradiated with gamma rays at 3.125 kGy, 6.25 kGy, 12.5 kGy or 25 kGy under wet conditions. Subsequently, the suspension was frozen at −20° C. and freeze-dried. The resulting material was immersed in Dulbecco's phosphate-buffered saline at room temperature for 4 hours, and then subjected to a compression test. The results were shown in FIG. 6. The amount of irradiated gamma rays was plotted on an abscissa axis, and the stress at certain distortion rates (40%, 50%, or 60%) was plotted on a longitudinal axis. It was found that the amount of irradiated gamma rays was correlated with the stress in an exponential fashion. From the results of fitting by non-linear least-squares method, the relationship of "(Stress of the sample without gamma ray irradiation)×EXP (0.12×irradiated amount)" was obtained.

INDUSTRIAL APPLICABILITY

The porous composite of the present invention can be used as a biomaterial such as a filling material for bone, a scaffold material for regenerative medicine, or an artificial bone.

Although the present invention has been described with reference to specific embodiments, various changes and modifications obvious to those skilled in the art are possible without departing from the scope of the appended claims.

REFERENCE SIGNS LIST

1 . . . porous material;
11 . . . polystyrene film;
2 . . . porous composite;
21 . . . region resistant to bioabsorbability (cross-linking-advanced part);
22 . . . region with excellent bioabsorbability (cross-linking-non-advanced part);
31 . . . tapered circular cone.

The invention claimed is:

1. A porous composite comprising a calcium phosphate crystal and a collagen fiber at a weight ratio of 80:20 to 20:80, wherein (1) a bioabsorbability of the porous composite is graded, and (2) the density of the porous composite determined by gravimetric method is 300 to 1500 mg/cm$^3$.

2. The porous composite according to claim 1, wherein the gradation of bioabsorbability is represented by a strength ratio of two points in the porous composite, determined by an indentation test using a cylindrical probe with a diameter of 2 mm, and the strength ratio of the two points at a distortion rate of 30% is 1.5 or more.

3. The porous composite according to claim 1, wherein the bioabsorbability is continuously or discontinuously varied, the first piece of the composite having a higher bioabsorbability and the second piece of the composite having a lower bioabsorbability can be cut out of the porous composite, the gradation of bioabsorbability is represented by a ratio of bioabsorbabilities of the first piece to the second piece, and the ratio is 1.5 times or more.

4. The porous composite according to claim 3, wherein the bioabsorbability is a biodegradation rate determined by collagenase digestion, the biodegradation rate is represented by the following equation (I):

$$\text{Biodegradation rate} = (W_0 - W_t)/W_0 \times 100 \quad (I)$$

(wherein $W_0$ and $W_t$ is both a dry weight before immersion and after immersion respectively, when the pieces of the porous composite are immersed in a collagenase solution of 2 unit/mL for 6 hours or in a collagenase solution of 200 units/mL for 30 minutes), the first piece is cut out of a region of 30% by weight of the porous composite having a higher biodegradation rate, the second piece is cut out of a region of 30% by weight of the porous composite having a lower biodegradation rate, and a ratio of biodegradation rates of the first piece to the second piece is 1.5 times or more.

5. The porous composite according to claim 3, wherein the bioabsorbability is denoted by a swelling ratio, the swelling ratio is represented by the following equation (II):

$$\text{Swelling ratio} = (W_w - W_d)/W_d \times 100 \quad (II)$$

(wherein $W_d$ and $W_w$ is a dry weight ($W_d$) before immersion and a wet weight ($W_w$) after immersion respectively, when the pieces of the porous composite are immersed in a phosphate-buffered saline for 24 hours), the first piece is cut out of a region of 30% by weight of the porous composite having a higher swelling ratio, the second piece is cut out of a region of 30% by weight of the porous composite having a lower swelling ratio, and a ratio of swelling ratios of the first piece to the second piece is 1.5 times or more.

6. The porous composite according to claim 1, wherein calcium phosphate is at least one calcium phosphate selected from the group consisting of hydroxyapatite, monocalcium phosphate anhydrous, monocalcium phosphate hydrate, dicalcium phosphate anhydrous, dicalcium phosphate hydrate, octacalcium phosphate, and tricalcium phosphate.

7. An artificial bone comprising the porous composite according to claim 1.

8. A method for preparing a porous composite, comprising the steps of:
   (A) forming a porous material containing calcium phosphate and collagen, and
   (B) cross-linking the porous material in a gradient manner through a cross-linking treatment capable of varying cross-link density, to obtain a porous composite having at least two regions wherein the ratio of bioabsorbabilities thereof is 1.5 times or more.

9. The method for preparing a porous composite according to claim 8, wherein the porous material forming step (A) comprises the steps of:
   (1) crystallizing calcium phosphate, to obtain a suspension of crystals or surface-modified crystals of calcium phosphate,
   (2) forming a collagen fibril from a soluble collagen in a collagen solution, to obtain a collagen fiber suspension,
   (3) mixing the collagen fibers suspension and the suspension of calcium phosphate crystals, to obtain a mixed suspension of calcium phosphate crystals and collagen fibers, and
   (4) forming the porous material from the mixed suspension of calcium phosphate crystals and collagen fibers.

10. The method for preparing a porous composite according to claim 8, wherein the porous material forming step (A) is a step of mixing calcium phosphate-collagen composite fibers, and a buffered solution, to gelate and form a porous material.

11. The method for preparing a porous composite according to claim 8, wherein the cross-linking in the gradient cross-linking step (B) is a cross-linking by a glutaraldehyde vapor deposition method, and a diffusion amount of glutaraldehyde gas into the porous material is varied, to prepare the porous composite having at least two regions wherein the ratio of bioabsorbabilities thereof is 1.5 times or more.

12. The method for preparing a porous composite according to claim 8, wherein the cross-linking in the gradient cross-linking step (B) is a cross-linking via irradiation, and the amount of irradiation to the porous material is varied under wet conditions, to prepare the porous composite having at least two regions wherein the ratio of bioabsorbabilities thereof is 1.5 times or more.

13. The method for preparing a porous composite according to claim 12, wherein the surface of the calcium phosphate crystal is modified with molecules with vinyl groups.

14. The method for preparing a porous composite according to claim 12, wherein calcium phosphate is at least one calcium phosphate selected from the group consisting of hydroxyapatite, monocalcium phosphate anhydrous, monocalcium phosphate hydrate, dicalcium phosphate anhydrous, dicalcium phosphate hydrate, octacalcium phosphate, and tricalcium phosphate.

\* \* \* \* \*